(12) United States Patent
Weiner et al.

(10) Patent No.: US 8,558,027 B2
(45) Date of Patent: Oct. 15, 2013

(54) PRODUCTION OF MIXTURES OF METHYLENEDIANILINE AND ITS HIGHER HOMOLOGUES USING CALCINED METAL OXIDE-SILICA CATALYSTS

(75) Inventors: Heiko Weiner, Sanford, MI (US); David C. Molzahn, Midland, MI (US); Robert J. Gulotty, Jr., Midland, MI (US)

(73) Assignee: Dow Global Technologies Inc., Midland, TX (US)

( * ) Notice: Subject to any disclaimer, the term of this patent is extended or adjusted under 35 U.S.C. 154(b) by 183 days.

(21) Appl. No.: 13/058,603

(22) PCT Filed: Aug. 14, 2009

(86) PCT No.: PCT/US2009/053815
§ 371 (c)(1),
(2), (4) Date: Feb. 11, 2011

(87) PCT Pub. No.: WO2010/019844
PCT Pub. Date: Feb. 18, 2010

(65) Prior Publication Data
US 2011/0144368 A1 Jun. 16, 2011

Related U.S. Application Data

(60) Provisional application No. 61/088,927, filed on Aug. 14, 2008, provisional application No. 61/146,193, filed on Jan. 21, 2009.

(51) Int. Cl.
*C07C 211/00* (2006.01)
(52) U.S. Cl.
USPC ............................. 564/334; 564/331; 564/332
(58) Field of Classification Search
None
See application file for complete search history.

(56) References Cited

U.S. PATENT DOCUMENTS

| 5,049,536 | A |  | 9/1991 | Bellussi et al. |  |
|---|---|---|---|---|---|
| 5,241,119 | A |  | 8/1993 | Clerici et al. | 564/332 |
| 6,818,795 | B2 | * | 11/2004 | Perego et al. | 564/332 |
| 2003/0023116 | A1 |  | 1/2003 | Klein et al. |  |

FOREIGN PATENT DOCUMENTS

| CN | 1400965 | 3/2003 |
|---|---|---|
| EP | 1 055 663 | 11/2000 |
| JP | 63-112540 | 5/1988 |
| JP | 2001-26571 | 1/2001 |
| JP | 2003-522748 | 7/2003 |
| JP | 2003-529577 | 10/2003 |
| JP | 2004-513086 | 4/2004 |
| WO | 01/58847 | 8/2001 |
| WO | 01/74755 | 10/2001 |
| WO | 02/20458 | 3/2002 |

OTHER PUBLICATIONS

International Preliminary Report on Patentability and Written Opinion; PCT/US2009/053815; pp. 12, Feb. 24, 2011.
International Search Report International Application No. PCT/US2009/053815, dated Jan. 27, 2010, 5 pages.
European Office Action; Application No. 09 791 517.7-1211; pp. 7, Mar. 27, 2012.
Chinese Office Action and English translation; Application No. 200980140675.3; p. 15.
Office Action (translated) in Japanese Patent Application No. 2011-523188, 3 pages.

* cited by examiner

*Primary Examiner* — Sudhakar Katakam
(74) *Attorney, Agent, or Firm* — Baker Botts L.L.P.

(57) ABSTRACT

The present disclosure relates to compositions, systems, and methods of forming an amine (e.g., methylenedianiline (MDA)) using an acid catalyst including, for example, a metal oxide-silica catalyst calcined at temperature(s) of about ≥500° C. to form a solid acid silica-metal oxide catalyst. A metal oxide of a solid acid silica-metal oxide catalyst may comprise alumina. A process for making a solid acid silica-metal oxide catalyst may comprise calcining an amorphous alumina-silica material at temperature(s) of about ≥500° C. and/or under an anhydrous and/or inert atmosphere. A rearrangement reaction of the condensation product of aniline and formaldehyde in the presence of a solid acid silica-metal oxide catalyst may yield more MDA and/or more desirable isomer(s) of MDA than reactions performed with a corresponding catalyst calcined at temperature(s) of less than 500° C.

14 Claims, 6 Drawing Sheets

US 8,558,027 B2

PRODUCTION OF MIXTURES OF METHYLENEDIANILINE AND ITS HIGHER HOMOLOGUES USING CALCINED METAL OXIDE-SILICA CATALYSTS

RELATED APPLICATIONS

This application is a 371 U.S. national application of International Application Number PCT/US2009/053815 filed Aug. 14, 2009, which designates the United States; and claims the benefit of claims the benefit of U.S. Provisional Patent Application Ser. No. 61/088,927 filed Aug. 14, 2008 and 61/146,193 filed Jan. 21, 2009 which are incorporated by reference.

FIELD OF THE DISCLOSURE

The present disclosure relates in general to acid catalyzed reactions using solid acid catalysts, including metal oxide-silica catalysts. Additionally, the present disclosure relates to the production of amines.

BACKGROUND OF THE DISCLOSURE

Methylenedianiline (MDA) and/or a mixture of MDA and its higher homologues may be a feedstock used to produce methylene diphenyl diisocyanate (MDI), which in turn may be used in the synthesis of a series of polymers, for example polyurethanes, thermoplastic polymers, and epoxy resins.

Methylenedianiline may be produced from aniline or from one of its derivatives by condensation with formaldehyde in the presence of solutions of strong acids, such as hydrochloric acid, sulfuric acid, and/or phosphoric acid, to give an amine salt, which then may be neutralized with base (e.g., strong base). Thus, operating conditions required to produce a product with desired structural characteristics and without forming undesirable amounts of by-products, may require sizable quantities of strong acid. In addition, use of strong acids may necessitate use of corrosion resistant materials in the equipment. Such construction materials are often expensive. Further, neutralization of strong acids with strong bases may lead to formation of sizable quantities of salts, which must be disposed safely. These salts may also be contaminated by aromatic products, which need to be discharged, resulting in increased production costs. Additionally, substantial quantities of waste water may be generated by this process, requiring sizable processing capacity and treatment.

SUMMARY

Accordingly, a need has arisen for compositions, systems, and methods for producing amines (e.g., MDA and its higher homologues) with increased safety and/or at lower cost.

The present disclosure relates, according to some embodiments, to compositions, methods, and systems for performing an acid-catalyzed reaction including, for example, isomerization of hydrocarbons, formation of esters and ethers, catalytic dehydration of alcohols and ethers to olefins, aromatic alkylations and acylations, aminolysis, polymerizations, and the like. For example, the present disclosure relates to compositions, methods, and systems for producing one or more amines (e.g., MDA and its higher homologues) using one or more metal silica catalysts (e.g., solid metal oxide-silica catalysts ($MO_x$—$SiO_2$) in some embodiments.

A process for producing a methylenedianiline or a mixture of methylenedianiline and its higher homologues, in some embodiments, may comprise contacting a catalyst composition with aniline and formaldehyde under conditions (i) to form an aminal and (ii) to rearrange the aminal to form the methylenedianiline, wherein the catalyst composition comprises a solid acid silica-metal oxide catalyst. According to some embodiments, a mole ratio of metal oxide to silica may be from more than about 0.01 to about 0.5 (e.g., about 0.03 to about 0.5). A solid acid silica-metal oxide catalyst may comprise metal oxide selected from the group consisting of $Al_2O_3$, $TiO_2$, $GeO_2$, $SnO_2$, $ZrO_2$, $B_2O_3$, $Nb_2O_5$, $Ta_2O_5$, $V_2O_5$, $MoO_3$, $WO_3$, and combinations thereof, in some embodiments. A process may be performed, according to some embodiments, wherein (a) the metal oxide is $Al_2O_3$ and (b) the solid acid silica-metal oxide catalyst (i) is substantially free of a binding agent and (ii) has an $Al_2O_3/SiO_2$ weight ratio of from more than about 0 to about 1. In some embodiments, a solid acid silica-metal oxide catalyst may have an $Al_2O_3/SiO_2$ weight ratio of from about 0.05 to about 0.7 and/or from about 0.1 to about 0.5. A catalyst composition may comprise a binding agent, according to some embodiments.

A solid acid silica-metal oxide catalyst may comprise, in some embodiments, from about 5 wt % to about 60 wt % $Al_2O_3$, from about 10 wt % to about 50 wt % $Al_2O_3$, and/or from about 30 wt % to about 45 wt % $Al_2O_3$. According to some embodiments, a methylenedianiline formed may comprise 4,4'-methylenedianiline (e.g., at least about 40 weight percent). Reaction conditions (ii) to rearrange the aminal to form the methylenedianiline, may comprise a temperature of from about 40° to about 150° C. in some embodiments. Reaction conditions (ii) to rearrange the aminal to form the methylenedianiline, according to some embodiments, may comprise a catalyst loading of from about 5 wt % to about 15 wt %. In some embodiments, contacting aniline and formaldehyde may comprise contacting aniline and formaldehyde at a molar ratio of aniline to formaldehyde of from about 2/1 to about 5/1. Contacting an aminal and a catalyst may comprise contacting the aminal and the catalyst in a fixed bed reactor according to some embodiments. For example, contacting an aminal and a catalyst may comprise contacting a liquid comprising the aminal with a fixed bed reactor comprising the catalyst. The weight hourly space velocity may be from about 0.02 to about 10. Contacting an aminal and a catalyst may comprise contacting the aminal and the catalyst in a substantially anhydrous inert atmosphere according to some embodiments. An anhydrous inert atmosphere may comprise, in some embodiments, a gas selected from the group consisting of nitrogen, argon, helium, neon, krypton, radon, xenon, and combinations thereof. According to some embodiments, a solid acid silica-metal oxide catalyst may comprise less than about 1 weight or mole percent water.

A solid catalyst for producing a methylenedianiline, in some embodiments, may comprise a solid acid silica-metal oxide catalyst having plurality of acid sites, wherein the ratio of the strong Lewis acid sites to the weak Lewis acid sites is less than about 0.55. This ratio may be expressed as the fraction of acidity with pyridine desorption at greater than 300° C. divided by the fraction of acidity with pyridine desorption at less than 300° C.

A process for preparing a solid acid silica-metal oxide catalyst, in some embodiments, may comprise calcining at a temperature of at least about 500° C. an amorphous metal oxide-silica material having a metal oxide to silica weight ratio from more than about 0 to about 1; and forming the solid acid silica-metal oxide catalyst having a plurality of acid sites, wherein the ratio of the total strong acid sites to the total weak acid sites is less than about 0.55. This ratio may be expressed as the fraction of acidity with pyridine desorption at greater than 300° C. divided by the fraction of acidity with pyridine desorption at less than 300° C. According to some embodiments, the temperature of calcination may be from about 500° C. to about 900° C. and/or from about 650° C. to about 800° C. An amorphous metal oxide-silica material may comprise an alumina-silica material in some embodiments. An alumina-silica material for preparing a solid acid silica-metal oxide catalyst may be, according to some embodiments, substantially free of a binding agent. In some embodiments, a solid acid silica-metal oxide catalyst may have an $Al_2O_3/SiO_2$ weight ratio of from about 0.05 to about 0.7 and/or from about 0.1 to about 0.5. A process for preparing a solid acid silica-metal oxide catalyst may further comprise adding a binding agent according to some embodiments. A calcining process may be performed, in some embodiments, to produce a solid acid silica-metal oxide catalyst comprising from about 5 wt % to about 50 wt % $Al_2O_3$. According to some embodiments, a calcining process may include calcining a material from about 1 hour to about 24 hours and/or from about 3 hours to about 8 hours. According to some embodiments, a solid acid silica-metal oxide catalyst may comprise less than about 1 weight or mole percent water. A process for preparing a solid acid silica-metal oxide catalyst, in some embodiments, may comprise calcining the amorphous metal oxide-silica material under a substantially anhydrous inert atmosphere. A substantially anhydrous inert atmosphere may comprise a gas selected from the group consisting of nitrogen, argon, helium, neon, krypton, radon, xenon, and combinations thereof according to some embodiments.

The present disclosure, in some embodiments, relates to a 4,4'-methylenedianiline and higher homologues made by a process comprising (a) contacting an aniline and formaldehyde under conditions to form an aminal, and (b) contacting the aminal with a catalyst composition to rearrange the aminal to form the 4,4'-methylenedianiline and higher homologues, wherein the catalyst composition comprises a calcined acid alumina-silica catalyst. In addition, the disclosure relates, according to some embodiments, to a 4,4'-methylene diphenyl diisocyanate and higher homologues made by a process comprising (a) contacting an aniline and formaldehyde under conditions to form an aminal, (b) contacting the aminal with a catalyst composition to rearrange the aminal to form the 4,4'-methylenedianiline and higher homologues, wherein the catalyst composition comprises a solid acid silica-metal oxide catalyst, and (c) contacting the 4,4'-methylenedianiline and higher homologues with a phosgene under conditions to form the 4,4'-methylene diphenyl diisocyanate and higher homologues. In some embodiments, the present disclosure further relates to a polyurethane made by a process comprising (a) contacting an aniline and formaldehyde under conditions to form an aminal, (b) contacting the aminal with a catalyst composition to rearrange the aminal to form the 4,4'-methylenedianiline and higher homologues, wherein the catalyst composition comprises a solid acid silica-metal oxide catalyst, (c) contacting the 4,4'-methylenedianiline and higher homologues with phosgene under conditions to form a 4,4'-methylene diphenyl diisocyanate and higher homologues, and (d) contacting the 4,4'-methylene diphenyl diisocyanate and higher homologues with a polyol under conditions to form the polyurethane.

BRIEF DESCRIPTION OF THE DRAWINGS

Some embodiments of the disclosure may be understood by referring, in part, to the present disclosure and the accompanying drawings, wherein.

DETAILED DESCRIPTION

Figure 1:
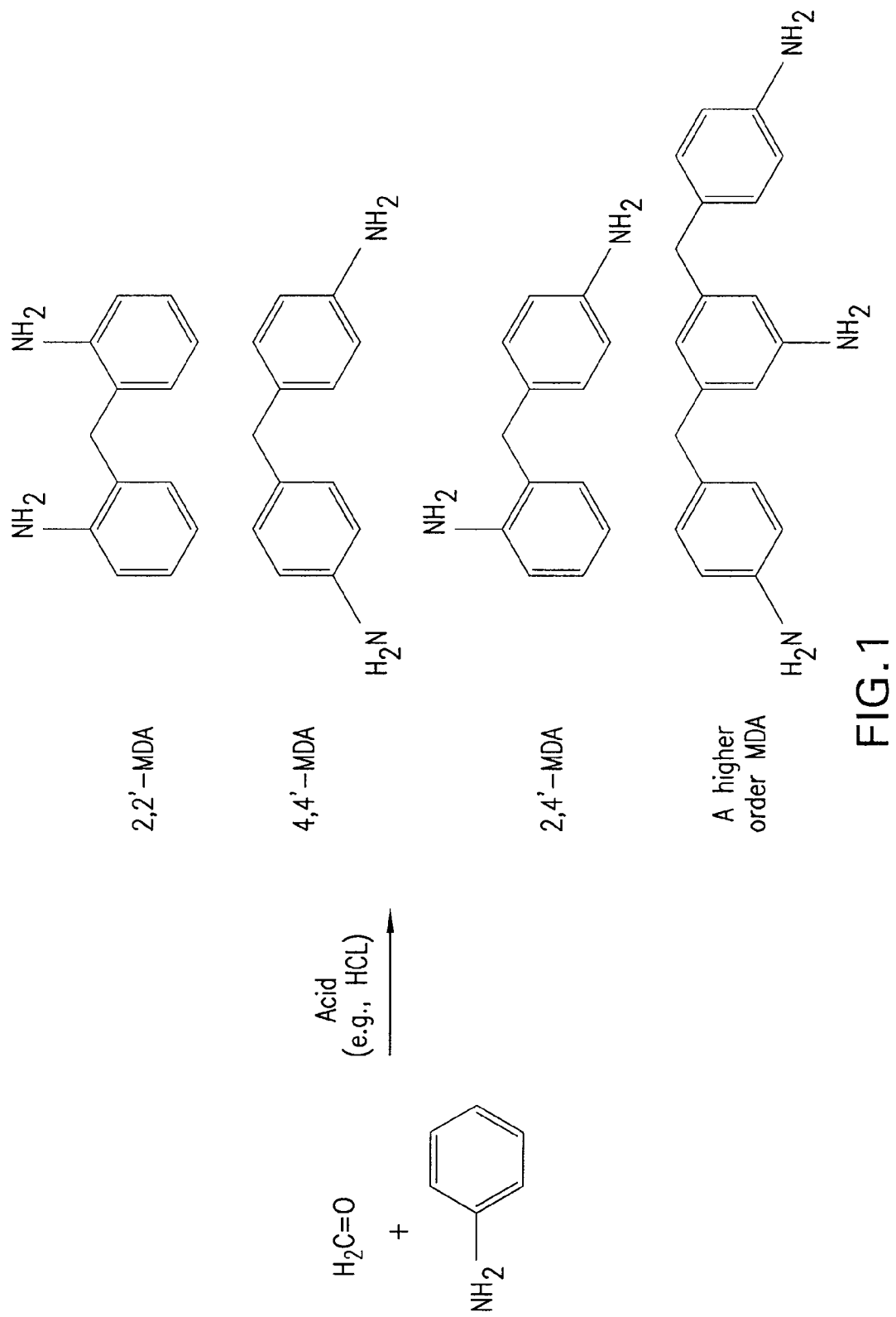
FIG. 1 illustrates a specific example embodiment of a condensation reaction between aniline and formaldehyde in the presence of an acid catalyst including a non-limiting set of 4 example products, 2,2'-MDA, 2,4'-MDA, 4,4'-MDA, and (3-ring) higher order MDA product (stoichiometry omitted)

The present disclosure relates to the use of catalyst compositions in acid catalyzed reactions according to some embodiments. The present disclosure relates, in some embodiments, to compositions, methods, and systems for producing one or more amines (e.g., MDA and its higher homologues) using one or more metal silica catalysts (e.g., solid metal oxide-silica catalysts ($MO_x$—$SiO_2$)). For example, the present disclosure relates, in some embodiments, to solid metal oxide-silica catalysts, $MO_x$—$SiO_2$. A solid metal oxide-silica catalyst may be anhydrous, according to some embodiments.

Compositions, systems, and/or processes for the synthesis of MDA and/or a mixture of MDA and its higher homologues, according to some embodiments of the disclosure, may reduce or eliminate significant costs, for example, by using a solid acid catalyst instead of a strong acid, like hydrochloric acid. Processes for producing a solid metal oxide-silica catalyst and/or processes for producing MDA and/or higher homologues may be performed under inert conditions including, for example, an anhydrous vacuum and/or an inert atmosphere. In some embodiments, compositions, systems, and/or processes may produce more of one MDA isomer (e.g., 4,4'-methylenedianiline) than another/others. In some embodiments, the present disclosure relates to a process for the production of MDA and/or a mixture of MDA and its higher homologues, by contacting an acid $MO_x$—$SiO_2$ catalyst (e.g., an alumina-silica catalyst calcined at high temperatures displaying Lewis and/or Brønsted acidity) with aniline and formaldehyde. Additionally, some embodiments of the disclosure relate to the production of (a) 4-4'-methylenedianiline, (b) 4-4'-methylene diphenyl diisocyante (e.g., by contacting the 4,4'-methylenedianiline and higher homologues with phosgene), and/or (c) polyurethanes (e.g., by contacting the 4-4'-methylene diphenyl diisocyante with polyols).

Catalyst Calcination

The disclosure additionally relates, according to some embodiments, to solid metal oxide-silica catalysts calcined at high temperature (e.g., over about 500° C.) and processes for producing them. In some embodiments, an increase in catalytic activity may be observed with increasing calcination temperatures.

Generally, metal oxide-silica catalysts, $MO_x$—$SiO_2$, may be calcined at low temperatures. As the calcination temperature rises to about 500° C. or higher, one may have expected to observe a decrease in catalytic activity. For example, a $MO_x$—$SiO_2$ catalyst calcined at 650° C. may have less activity in cracking neopentane than a $MO_x$—$SiO_2$ catalyst calcined at 500° C. According to some embodiments of the disclosure, however, a solid acid silica-metal oxide catalyst may be prepared by calcining raw material at ≥about 500° C. (e.g., from about 650° C. to about 750° C.).

A solid acid silica-metal oxide catalyst, in some embodiments, may have higher activity in one or more acid-catalyzed reactions (e.g., reactions with nitrogen groups) than a corresponding metal oxide-silica catalyst calcined at a lower temperature (e.g., ≤500° C., ≤450° C., ≤400° C., ≤350° C., ≤300° C., and/or ≤250° C.). In some embodiments, a high temperature calcined metal oxide-silica catalyst (e.g., a solid acid silica-metal oxide catalyst) may be recovered and regenerated with little or no decrease in activity compared to fresh material. An increase in selectivity towards the 4,4'-methylenedianiline isomer may be observed in the synthesis of MDA from aniline and formaldehyde according to some embodiments. A two-fold or higher increase in activity may be observed, in some embodiments, by increasing the calcination temperature from about 500° C. to about 750° C., without an apparent loss in selectivity towards a 4,4'-methylenedianiline isomer.

Without limiting any particular embodiment to any particular theory or mechanism of action, it may be that higher calcination temperatures bring about a desirable and/or optimal balance between acid sites of various binding affinities in the catalyst. For example, lower calcination temperatures may produce a catalyst with a higher density of strong acid sites that may tightly bind amines and/or polyamines to the catalyst surface. This may reduce activity and/or lead to unwanted side reactions. Again, without limiting any particular embodiment to any particular theory or mechanism of action, higher calcination temperatures may produce a catalyst with a lower density of strong acid sites allowing reactants and/or products to more readily move on and off the catalyst.

A catalyst (e.g., a solid acid metal oxide-silica catalyst displaying Lewis and/or Brønsted acidity) may be prepared, in some embodiments, at a constant or variable temperature ≥about 500° C., ≥about 550° C., ≥about 600° C., ≥about 650° C., ≥about 700° C., ≥about 750° C., ≥about 800° C., ≥about 850° C., ≥about 900° C., and/or ≥about 950° C. In some embodiments, catalysts may be calcined at a temperature from about 500° C. to about 900° C. (e.g., from about 500° C. to about 800° C. and/or from about 650° C. to about 750° C.). A catalyst (e.g., a solid acid silica-metal oxide catalyst) may be calcined for a duration from about 1 hour to about 24 hours. For example, calcination duration may be from about 3 hours to about 8 hours. In some embodiments, a catalyst may be calcined at a temperature below about 500° C. before or after being calcined at a temperature at or above about 500° C. A catalyst may be calcined, according to some embodiments, under inert conditions. For example, a catalyst may be calcined anhydrously under an inert gas (e.g., under argon, nitrogen, helium, neon, and the like).

According to some embodiments, (a) calcining an amorphous silica-alumina-based material and/or a zeolite Y-based material under inert gas in a tube furnace and/or (b) transferring the resulting anhydrous materials into a Vacuum-Atmospheres dry box for catalytic evaluation under inert (anhydrous) conditions may improve catalytic activity (e.g., ≥10%, ≥20%, ≥30%, and/or ≥40%) relative to materials prepared in the presence of ambient moisture. Improved catalytic activity may be observed, in some embodiments, substantially without a loss and/or change in specificity.

Catalyst Composition

A solid acid silica-metal oxide catalyst may include, for example, extrudates and powders. A solid acid silica-metal oxide catalyst, in some embodiments, may be substantially free of a zeolite. In some embodiments, a catalyst may include an alumina-silica zeolite having a faujasite (FAU) structure (e.g., zeolite Y). A catalyst, according to some embodiments, may include a polyoxometalate-based solid acid (e.g., $H_3PM_{12}O_{40}$ (M=Mo, W), $H_4SiM_{12}O_{40}$ (M=Mo, W)), soluble salts thereof, insoluble salts thereof, and the like, and combinations thereof. In some embodiments, a solid acid silica-metal oxide catalyst may comprise silicon (e.g., silica) one or more metals (e.g., as an oxide). Examples of metal oxides may include, without limitation, $Al_2O_3$, $TiO_2$, $GeO_2$, $SnO_2$, $ZrO_2$, $B_2O_3$, $Nb_2O_5$, $Ta_2O_5$, $V_2O_5$, $MoO_3$, $WO_3$, and the like.

A solid acid silica-metal oxide catalyst may be prepared, in some embodiments, from one or more amorphous silica-alumina materials. For example, an amorphous silica-alumina material may include sodium silicate, sodium aluminate (e.g., solids or solutions), colloidal silica, aluminum salts (e.g., nitrates and sulfates), silicon and aluminum alkoxides, and the like. An amorphous silica-alumina material may be used for the preparation of silica-alumina materials with various Si/Al ratios, according to some embodiments. For example, in some embodiments, a solid acid silica-metal oxide catalyst may comprise and/or may be prepared from one or more of the following amorphous alumina-silica materials:

(1) DAVICAT® SIAL 3111 ($SiO_2$, 85.7%; $Al_2O_3$, 11.3%, Density, 0.35 g/cc; Pore Volume, 1.15 cc/g; BET Surface Area, 424 m²/g);

(2) DAVICAT® SIAL 3113 ($SiO_2$, 84.9%; $Al_2O_3$, 14.4%, Density, 0.5 g/cc; Pore Volume, 0.76 cc/g; BET Surface Area, 573 m²/g);

(3) DAVICAT® SIAL 3125 ($SiO_2$, 74.6%; $Al_2O_3$, 24.1%, Density, 0.49 g/cc; Pore Volume, 0.79 cc/g; BET Surface Area, 552 m²/g);

(4) Alcoa® Hi Q20 (Binder) ($Al_2O_3$, 72%, Bulk Density, 670-750 g/L; Pore Volume, 0.4-0.5 cc/g; BET Surface Area, 424 m²/g); and (5) materials comprising from about 2 weight percent to about 46 weight percent $Al_2O_3$ with various pore volumes and surface areas (prepared from silicon and aluminum alkoxides, e.g., tetraethoxysilane (TEOS), aluminum isopropoxide, di-s-butoxyaluminoxytriethoxysilane).

In some embodiments, a solid acid silica-metal oxide catalyst may comprise silica and a metal as an oxide at an atomic ratio of silica to metal ("a Si:M ratio") of from about 1 to about 15. For example, a Si:M ratio may be about 2.3. A solid acid silica-metal oxide catalyst may have a SiO$_2$:MOx ratio of from more than about 2 to about 10. The relative amounts of metal oxide to silica may also be expressed in terms of weight percents. For example, a solid acid silica-metal oxide catalyst comprising Al$_2$O$_3$ and silica may have from about 0 (e.g., approaching 0) to about 50 weight percent Al$_2$O$_3$, from about 2.5 to about 40 weight percent Al$_2$O$_3$, and/or from about 5 to about 35 weight percent Al$_2$O$_3$ and/or from about 100 (e.g., approaching 100) to about 50 weight percent SiO$_2$, from about 98 to about 60 weight percent SiO$_2$, and/or may have from about 90 to about 70 weight percent SiO$_2$.

A solid acid silica-metal oxide catalyst may have a lower density of strong acid sites than a corresponding metal oxide-silica catalyst calcined at a temperature ≤500° C., ≤450° C., ≤400° C., ≤350° C., ≤300° C., and/or ≤250° C. in some embodiments. Acidity of a catalyst may be assessed, according to some embodiments, using pyridine absorption and infrared spectroscopy. Acid site density of catalysts according to some embodiments of the disclosure were analyzed by pyridine sorption. Reduction in acid density with increases in calcination temperature is demonstrated in FIG. 4, and Example 10. In some embodiments, the total acidity of a solid acid silica-metal oxide catalyst may be from about 25% to about 50% lower than an uncalcined (e.g., calcined at room temperature) amorphous metal oxide-silica catalyst.

A solid acid silica-metal oxide catalyst may have a lower ratio of strong acid sites to weak acid sites than an uncalcined (e.g., calcined at room temperature) amorphous metal oxide-silica catalyst in some embodiments. This ratio may be expressed as the fraction of acidity with pyridine desorption at greater than 300° C. divided by the fraction of acidity with pyridine desorption at less than 300° C. This ratio for a solid acid silica-metal oxide catalyst may be less than about 0.6, less than about 0.5, less than about 0.4, less than about 0.3, and/or less than about 0.25.

In some embodiments, a catalyst (e.g., a solid acid silica-metal oxide catalyst) may be substantially free of a binding agent. Catalysts may be in powder form, which may be used in slurry reactions. In some embodiments, a catalyst (e.g., a solid acid silica-metal oxide catalyst) that is substantially free of a binding agent may include Al$_2$O$_3$ at a weight percent of from about 0 (e.g., approaching 0) to about 50 (e.g., from about 5 wt % to about 40 wt % and/or from about 10 wt % to about 35 wt %) and/or SiO$_2$ at a weight percent of from about 100 (e.g., approaching 100) to about 50 (e.g., from about 95 wt % to about 60 wt % and/or from about 90 wt % to about 65 wt %).

In some embodiments, a solid acid silica-metal oxide catalyst may include a binder (e.g., an alumina-based binder and/or a clay). A non-limiting example of a commercially-available binding agent is Alcoa® Hi Q20. A calcined Lewis-acid metal oxide silica catalyst comprising a binder may be extruded to form a catalyst for heterogeneous reactions (e.g., reactions in which the catalyst and the product are in different physical phases), according to some embodiments. A catalyst may be pelletized. In some embodiments, a catalyst (e.g., a solid acid silica-metal oxide catalyst) that includes a binding agent may include Al$_2$O$_3$ at a weight percent of from about 5 to about 60 (e.g., from about 10 wt % to about 50 wt % and/or from about 15 wt % to about 45 wt %) and/or SiO$_2$ at a weight percent of about 95 to about 40 (e.g., from about 90 wt % to about 50 wt % and/or from about 85 wt % to about 70 wt %).

General Catalyst Properties

According to some embodiments, a solid acid silica-metal oxide catalyst may have long-term stability. For example, a solid acid silica-metal oxide catalyst may maintain its catalytic activity for over about 100 hours, over about 200 hours, over about 300 hours, over about 400 hours, over about 500 hours, over about 600 hours, over about 700 hours, and/or over about 800 hours. Calcining a metal oxide-silica material at high temperatures, in some embodiments, may produce a solid acid silica-metal oxide catalyst with increased long-term stability and catalyst activity relative to, for example, untreated materials or materials calcined at lower temperatures (e.g., ≤500° C., ≤450° C., ≤400° C., ≤350° C., ≤300° C., and/or ≤250° C.).

In some embodiments, a catalyst may have little or no bound water and/or be dehydroxylated to a greater extent by calcination compared to a catalyst that has not been calcined or that has been re-hydroxylated by ambient moisture. For example, a Davicat 135 silica alumina material that has not been recently calcined may contain 4-7% moisture content relative to a Davicat 135 silica alumina that has been calcined to 700° C. and maintained in an anhydrous environment. The catalyst that has moisture content similar to the catalyst when calcined at 700° C. and maintained in an anhydrous environment may have a higher catalyst activity for the MDA reaction than a material which has picked up moisture and been re-hydroxylated.

A catalyst (e.g., a catalyst extrudate), according to some embodiments, may be used in a fixed bed reactor. A system for forming an MDA may include, in some embodiments, a fixed bed reactor.

Acid Catalyzed Reactions

In some embodiments of the disclosure, a reaction (e.g., an aminal to MDA rearrangement reaction) may be performed as a continuous or a batch reaction. In some embodiments, the disclosure provides a process for producing MDA and/or a mixture of MDA and its higher homologues from aniline and formaldehyde. Processes may include contacting solid acid silica-metal oxide catalysts with aniline and formaldehyde under conditions such that a condensation reaction forms aminal and a rearrangement reaction of aminal forms MDA and/or a mixture of MDA and its higher homologues. In some embodiments, conditions may include conducting a reaction at a temperature from about 40° C. to about 150° C. According to some embodiments, a reaction may be conducted at a temperature from about 60° C. to about 150° C. (e.g., from about 60° C. to about 120° C.). A reaction may be conducted in the presence of an inert gas (e.g., to the substantial exclusion of water).

According to some embodiments, a homogeneous reaction (e.g., to rearrange an aminal to MDA) may be performed at a temperature of from about 40° C. to about 150° C. (e.g., from about 40° C. to about 150° C., from about 50° C. to about 140° C., and/or from about 60° C. to about 120° C.). A catalytic reaction (e.g., a homogeneous reaction to rearrange an aminal to MDA) may be performed, in some embodiments, at an aniline to formaldehyde molar ratio of from about 2/1 to about 10/1 (e.g., from about 2/1 to about 5/1 and/or from about 5/1 to about 10/1). A catalytic reaction (e.g., a homogeneous reaction to rearrange an aminal to MDA) may be performed at a catalyst loading (100×(wt of catalyst)/(wt of reactant solution)) of from about 0.01 weight percent to about 5.0 weight percent (e.g., from about 0.1 weight percent to about 3.0 weight percent and/or from about 0.5 weight percent to about 2.0 weight percent).

According to some embodiments, a heterogeneous reaction (e.g., to rearrange an aminal to MDA) may be performed at a temperature of from about 40° C. to about 150° C. (e.g., from about 40° C. to about 150° C., from about 50° C. to about 140° C., and/or from about 60° C. to about 120° C.). A catalytic reaction (e.g., a heterogeneous reaction to rearrange an aminal to MDA) may be performed, in some embodiments, at an aniline to formaldehyde molar ratio of from about 1/1 to about 10/1 (e.g., from about 5/1 to about 10/1, from about 2/1 to about 5/1, and/or from about 2/1 to about 4/1). A catalytic reaction (e.g., a homogeneous reaction to rearrange an aminal to MDA) may be performed at a catalyst loading of from about 0.2 weight percent to about 30 weight percent (e.g., from about 1 weight percent to about 30 weight percent, from about 2 weight percent to about 20 weight percent, and/or from about 5 weight percent to about 15 weight percent). In some embodiments, a catalytic reaction may be performed as a fixed bed process. The weight hourly space velocity (e.g., weight of liquid per weight or volume of catalyst per hour) may be, for example, less than about 10, more than about 0.1, and/or more than about 0.02. A process may comprise, according to some embodiments, condensing aniline and formaldehyde to form aminal substantially in the absence of a halide.

In some embodiments, MDA formed may comprise 4,4'-methylenedianiline and higher homologues. Furthermore, MDA formed may comprise at least about 40 weight percent 4,4'-methylenedianiline, at least about 45 weight percent 4,4'-methylenedianiline, at least about 50 weight percent 4,4'-methylenedianiline, at least about 55 weight percent 4,4'-methylenedianiline, at least about 60 weight percent 4,4'-methylenedianiline, at least about 65 weight percent 4,4'-methylenedianiline, and/or at least about 70 weight percent 4,4'-methylenedianiline. Additionally, mixtures of MDA and its higher homologues formed may comprise at least about 40 weight percent 4,4'-methylenedianiline. Of the two ring MDA fraction, the weight of 4,4'-methylenedianiline may be over about 80%.

In some embodiments, the disclosure relates to a process for producing 4,4'-methylenedianiline and higher homologues by condensing aniline and formaldehyde to form aminal, and contacting the aminal with a solid acid silica-metal oxide catalyst under conditions that permit formation of 4,4'-methylenedianiline and higher homologues (e.g., by a rearrangement reaction of aminal). Furthermore, the disclosure relates to a process for formation of 4,4'-methylene diisocyante by condensing aniline and formaldehyde to form aminal, contacting the aminal with a solid acid silica-metal oxide catalyst under conditions the permit formation of 4,4'-methylenedianiline and higher homologues (e.g., by a rearrangement reaction of aminal), and contacting 4,4'-methylenedianiline and higher homologues with phosgene to form 4,4'-methylene diisocyante and higher homologues.

The disclosure, according to some embodiments, relates to a process for formation of a polyurethane by contacting solid acid silica-metal oxide catalysts with aniline and formaldehyde under conditions such that a condensation reaction forms aminal, a rearrangement reaction of aminal forms 4,4'-methylenedianiline and higher homologues, a reaction of the 4,4'-methylenedianiline and higher homologues with phosgene forms 4,4'-methylene diisocyante, and a reaction of 4,4'-methylene diisocyante with a polyol forms polyurethane.

In some embodiments, the disclosure relates to processes for recovery and regeneration of solid acid silica-metal oxide catalysts using a hot reactant wash, including a hot solvent wash (e.g., a hot aniline wash), followed by re-calcination. Regeneration may include, for example, contacting (e.g., washing) a catalyst (e.g., a partially exhausted catalyst) with an aromatic compound (e.g., phenol, an aromatic amine, aniline) in at least a partially liquid phase. The temperature of regeneration may be higher than the condensation and/or rearrangement reaction temperature that produces an optionally substituted MDA. An aromatic compound may comprise a substituent having activating characteristics with respect to electrophilic substitution as compared to the aromatic compound without the said substituent.

A system for forming an MDA may include (a) a calcined Lewis-acid metal oxide-silica catalyst and (b) an aniline, a formaldehyde, and/or a reaction vessel. A reaction vessel may be an open or closed container and may comprise a heating/cooling system and/or a thermostat for maintaining a desired reaction temperature. A system for forming a methylene diisocyante may comprise a system for forming MDA plus phosgene. A system for forming a polyurethane may comprise a system for forming a methylene diisocyante plus a polyol.

EXAMPLES

Some embodiments of the disclosure may be illustrated by one or more of the following examples.

Example 1

Catalyst Synthesis: DSiAl-1 Extrudate (1/16)

750 g of DAVICAT® SIAL 3113, 250 g of Alcoa Hi Q20 (alumina binding agent) and 959.14 g of $H_2O$ were mixed, mulled for approximately 15 minutes at room temperature and extruded. The 1/16 extrudates were oven dried overnight at 80° C. under air. The dried pellets were split into three batches of 300 g each. Batch one was left as obtained, batch two was calcined at 300° C. for six hours, and batch three was calcined at 500° C. for six hours, all under air.

Example 2

Aminal (N,N'-Dianilinomethane) Preparation

The preparation was carried out under an inert gas atmosphere (argon). 3000 g of aniline (distilled over Zn powder) was placed in a 5 L round-bottomed flask (three-neck), equipped with a drop funnel, a thermometer, and a stir bar and cooled to 5° C. using an ice bath. 525 g of formalin solution (37% formaldehyde in $H_2O$) was then added to the aniline and stirred for greater than 30 minutes, keeping the temperature below 10° C.

The mixture was then allowed to warm up to room temperature and stirred for another four hours. The mixture was then placed in a separatory funnel under argon and left standing overnight at room temperature. The organic phase was then separated and dried over 120 g of anhydrous $MgSO_4$. The final product, containing the aminal in excess aniline (total aniline to formaldehyde molar ratio 5:1), was used for catalyst evaluation in batch reactions.

Example 3

Catalyst Evaluation (Batch Reaction): DSiAl-1 Extrudate 0.5 g of the DSiAl-1 extrudate (batch 3 from example 1, calcined at 500° C.) was placed in a 25 mL flask containing a magnetic stir bar. Next, 5.0 g of the aminal/aniline solution (example 2) was added. The mixture was heated to 60° C. and stirred for four hours at this temperature. After removing an aliquot of reaction solution for GC analysis, the mixture was heated to 95° C. and stirred for another two hours at this temperature. The final reaction mixture was evaluated by GC analysis.

Final Product composition (95° C.): 4,4'-MDA; 12.0 wt %; 2,4'-MDA: 1.3 wt %; N-o-Aminobenzyl aniline (OABA); 1.9 wt %; N-p-Aminobenzyl aniline (PABA); 10.2 wt %; Trimers and heavy components: 5.2 wt %.

Example 4

Catalyst Evaluation (Batch Reaction): DAVICAT® SIAL 3113

Catalyst evaluation was carried out according to example 3 using 0.5 g of DAVICAT® SIAL 3113 (powder) as the solid catalyst.

Final Product composition (95° C.): 4,4'-MDA; 11.4 wt %; 2,4'-MDA: 1.4 wt %; N-o-Aminobenzyl aniline (GABA); 1.8 wt %; N-p-Aminobenzyl aniline (PABA); 15.9 wt %; Trimers and heavy components: 14.9 wt %.

Example 5

Catalyst Evaluation (Batch Reaction): Alcoa Hi Q20

The activity of the binder material used for the preparation of the DSiAl-1 extrudate in example 1 was evaluated separately. Catalyst evaluation was carried out according to example 3 using 0.5 g of the Alcoa Hi Q20 binding agent (calcined at 500° C.) as the solid catalyst. The material was found inactive at both the 60° C. and 95° C. reaction temperatures.

Example 6

Figure 2:
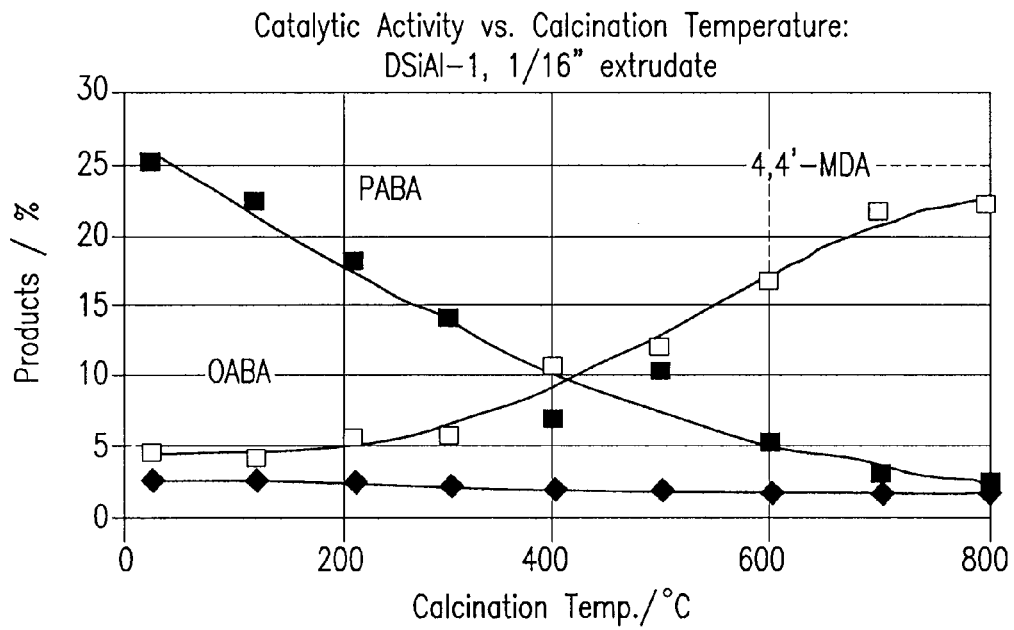
FIG. 2 illustrates catalytic activity at different calcination temperatures for an alumina silica extrudate containing a binder according to a specific example embodiment of the disclosure.

Catalyst Evaluation (Batch Reaction): DSiAl-1 Extrudate, Calcination Temperature/Activity Study 5 g samples of the DSiAl-1 extrudate (batch one from example 1, room temperature), prepared according to example 1, was calcined at various temperatures from room temperature to 800° C. for six hours under air and one atmosphere pressure. Catalyst evaluation was carried out according to example 3 using 0.5 g of the solid catalysts in each experiment. A significant activity increase was found with increasing calcination temperature. The activities for the room temperature sample and the calcined samples are shown below in Table 1 and illustrated in FIG. 2 (Reaction conditions: aminal/aniline (preparation using 5:1 molar ratio of aniline to formaldehyde), 5.0 mL; solid acid catalyst, 14/30 mesh, 0.5 g; (1) T=60° C./4 h, (2) T=95° C./2 h; 1 atm Ar.).

TABLE 1

| T/° C. | Products/wt % | | | | |
|---|---|---|---|---|---|
| | 4,4'-MDA | 2,4'-MDA | OABA | PABA | Oligomers |
| 25 | 4.55 | 0.43 | 2.69 | 25.20 | 4.65 |
| 120 | 4.16 | 0.44 | 2.59 | 22.36 | 4.29 |
| 210 | 5.42 | 0.58 | 2.41 | 18.01 | 4.91 |
| 300 | 6.01 | 0.66 | 2.23 | 13.95 | 4.62 |
| 400 | 10.61 | 1.09 | 1.80 | 6.90 | 4.38 |
| 500 | 12.00 | 1.28 | 1.89 | 10.24 | 5.19 |
| 600 | 16.52 | 1.82 | 1.71 | 5.27 | 5.28 |
| 700 | 21.60 | 2.46 | 1.69 | 3.03 | 16.53 |
| 800 | 22.26 | 2.54 | 1.61 | 2.44 | 15.38 |

Example 7

Figure 3:
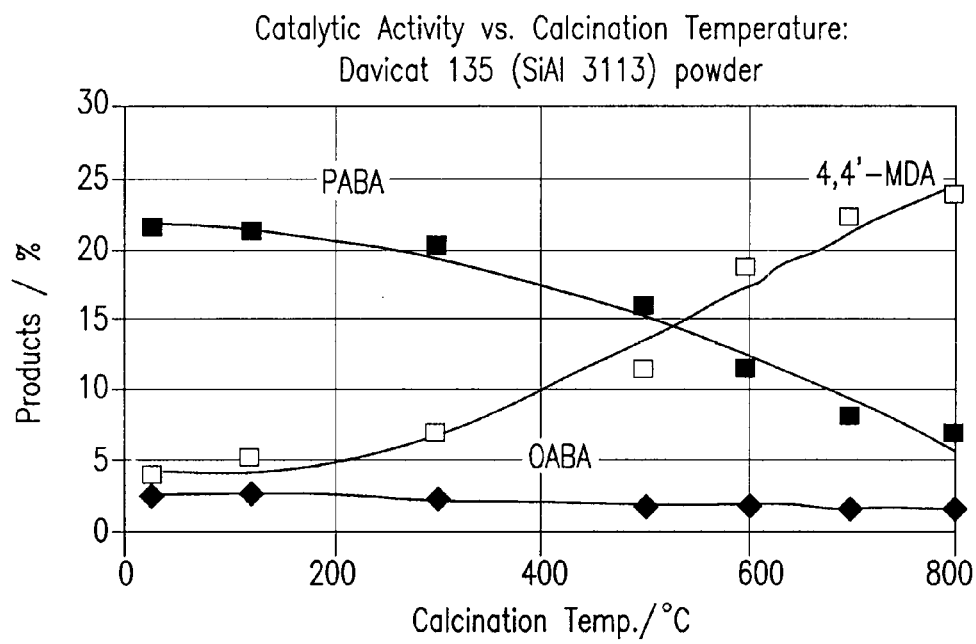
FIG. 3 illustrates catalytic activity at different calcination temperatures for an alumina silica powder without a binder according to a specific example embodiment of the disclosure.

Catalyst Evaluation (Batch Reaction): DAVICAT® SIAL 3113, Calcination Temperature/Activity Study The catalytic activity of the binder-free, DAVICAT® SIAL 3113 (powder, used in the preparation of the DSiAl-1 extrudate according to example 1), was evaluated vs. the calcination temperature. Sample calcination and activity measurements were carried out according to example 6 using calcined samples of DAVICAT® SIAL 3113 (powder) as the solid catalysts. A significant activity increase was found with increasing calcination temperature. The activities for the room temperature sample and the sample calcined at 800° C. are shown below and illustrated in FIG. 3 (Reaction conditions: aminal/aniline (preparation using 5:1 molar ratio of aniline to formaldehyde), 5.0 mL; solid acid catalyst, 14/30 mesh, 0.5 g; (1) T=60° C./4 h, (2) T=95° C./2 h; 1 atm Ar.).

Room Temperature: Product composition (95° C.): 4,4'-MDA: 3.8 wt %; 2,4'-MDA: 0.3 wt %; N-o-Aminobenzyl aniline (OABA): 2.6 wt %; N-p-Aminobenzyl aniline (PABA): 21.3 wt %; Trimers and heavy components: 11.8 wt %.

Calcined at 800° C.: Product composition (95° C.): 4,4'-MDA: 23.8 wt %; 2,4'-MDA: 2.1 wt %; N-o-Aminobenzyl aniline (OABA): 1.7 wt %; N-p-Aminobenzyl aniline (PABA): 7.1 wt %; Trimers and heavy components: 13.4 wt %.

Example 8

Catalyst Evaluation (Batch Reaction): Lewis Acid Catalysts, $Ln(CF_3SO_3)_3$ The catalytic activity of homogeneous Lewis acid catalysts was evaluated using several lanthanide triflates, $Ln(trif)_3$ (Ln=Sc, Eu, Yb, Sm, Pr; trif=trifluoremethane sulfonate, $CF_3SO_3$) as specific examples, which are provided by way of illustration and not as limitations on the scope of this disclosure. Catalyst evaluation was carried out according to example 3 using 0.1 g (1 wt %) of the triflate catalysts and 10.0 g of the aminal/aniline solution (example 2). All materials exhibited high catalytic activity, the data summary is provided in Table 2.

TABLE 2

| | | | Product Composition (wt %) | | | | |
|---|---|---|---|---|---|---|---|
| Entry No. | Catalyst[a] | MW (g/mol) | 4,4'-MDA | 2,4'-MDA | OABA | PABA | Polymeric |
| 1 | $Sc(CF_3SO_3)_3$ | 492.16 | 23.8 | 4.5 | 0.28 | — | 3.7 |
| 2 | $Eu(CF_3SO_3)_3$ | 599.16 | 22.0 | 4.1 | 0.26 | — | 4.4 |
| 3 | $Yb(CF_3SO_3)_3$ | 620.24 | 20.7 | 4.1 | 0.28 | — | 4.4 |
| 4 | $Sm(CF_3SO_3)_3$ | 597.56 | 22.2 | 4.2 | 0.26 | — | 4.6 |
| 5 | $Pr(CF_3SO_3)_3$ | 588.11 | 22.1 | 4.1 | 0.26 | — | 4.6 |

[a]Water-tolerant Lewis acid

Example 9

Condensation Reaction

Aniline and formaldehyde at a weight ratio of 5:1 may be contacted with a solid acid silica-metal oxide catalyst under conditions that permit MDA formation. This reaction may be allowed to run to completion, at which time the product solution may comprise about 59% aniline by weight. Using a 60 C/95 C reaction condition and running to full conversion of aminal and PABA, the product solution may include about 28 weight % 4,4'-MDA and about 5 weight % 2,4'-MDA+OABA. The balance of the product solution (~8 weight %) may include higher order MDAs (e.g., MDAs comprising 3, 4, 5, or 6 rings). The selectivity for 4,4'-MDA relative to 2,2'-MDA and 2,4'-MDA may be over 80% (e.g., 83-87%).

Example 10

Effect of Calcination Temperature on Lewis and Brønsted Acidity

Absorbance at 1455 $cm^{-1}$ corresponds to the number of coordinately bound molecules of pyridine (i.e., Lewis acid sites), whereas absorbance at 1540 $cm^{-1}$ corresponds to the number of pyridinium ions present (i.e., Brønsted acid sites). Thus, changes in absorbance as a function of temperature provide an indication of the relative number and/or strength of acid sites present on the catalyst.

Lewis and Brønsted acidity of alumina-silica catalysts prepared at calcination temperatures of room temperature (control), 500° C., and 700° C. according to Example 1 (DSiAl-1) was analyzed by infrared spectroscopy of adsorbed pyridine. A catalyst wafer suitable for infrared analysis was prepared. The sample was placed into the measurement cell and heated to 400° C. to dehydrate the sample and then cooled at 150° C. under flowing nitrogen. 5 microliters of pyridine were injected into the gas stream passing over the catalyst. After 5 minutes an IR spectrum was recorded. Then, another 5 microliter injection of pyridine was made and after 5 minutes another IR spectrum was recorded. If successive IR spectra are substantially identical then the experiment proceeds to the next step, otherwise another injection of pyridine is made. IR spectra were then recorded as a function of temperature up to a final temperature of 400° C. Results are shown in Table 3 and FIG. 4.

In Table 3, there is a decrease in the amount of pyridine adsorbed as the treatment temperature is increased. Both Lewis and Bronsted site numbers decrease, however, the number of Lewis sites decreases more, resulting in a higher Bronsted to Lewis ratio for the sample treated at the highest temperature.

TABLE 3

| Catalyst | IR Absorbance (Lewis acidity, (~1455 $cm^{-1}$)) | IR Absorbance (Brønsted acidity (~1540 $cm^{-1}$)) | Ratio of Brønsted to Lewis sites |
|---|---|---|---|
| RT (Control) | 0.258 | 0.054 | 0.209 |
| 500 | 0.185 | 0.042 | 0.227 |
| 700 | 0.132 | 0.032 | 0.242 |

Figure 4:
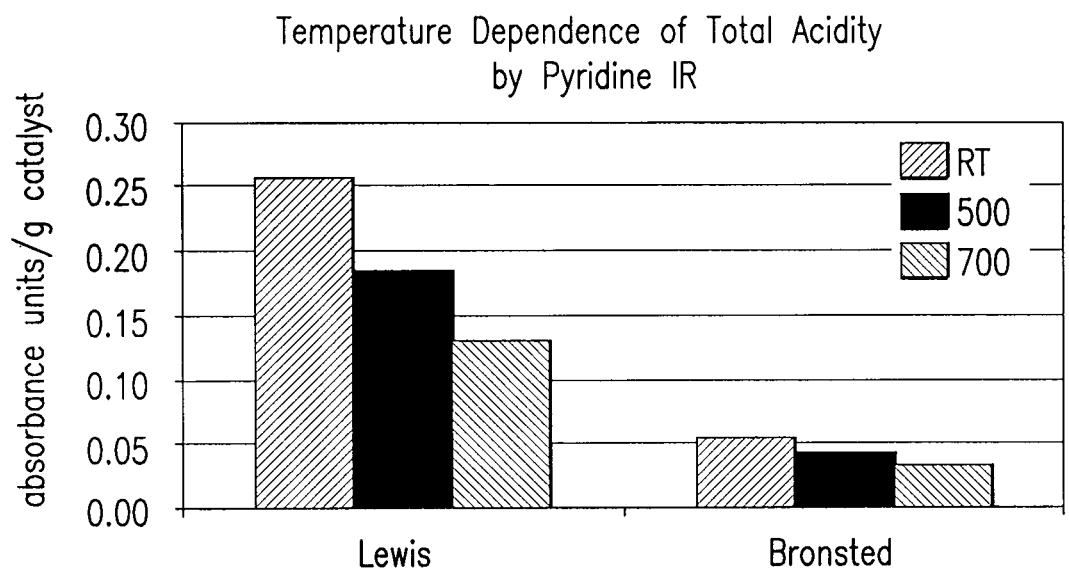
FIG. 4 is a bar graph illustrating infrared absorbance (in arbitrary units based on peak height absorbance at 1455 cm$^{-1}$ for Lewis acidity and 1540 cm$^{-1}$ for Bronsted acidity) per gram of catalyst for catalyst materials exposed to pyridine vapors according to specific example embodiments of the disclosure.

As illustrated in FIG. 4, the control catalyst (calcined at room temperature) displayed the highest absorbance at 1455 $cm^{-1}$ per gram of the three catalysts indicating that it had the most Lewis acid sites (FIG. 4, left side). The catalyst calcined at 700° C. displayed the lowest absorbance at 1455 $cm^{-1}$ of the three catalysts indicating that it had the fewest Lewis acid sites.

The catalyst calcined at room temperature also displayed the highest absorbance at 1540 $cm^{-1}$ per gram of the three catalysts tested indicating that it had the most Brønsted acid sites (FIG. 4, right side). The catalyst calcined at 700° C. displayed the lowest absorbance at 1540 $cm^{-1}$ of the three catalysts indicating that it had the fewest Brønsted acid sites. However, as FIG. 4 shows, the degree of difference between the Brønsted acidity of the three catalysts was smaller than the degree of difference between the Lewis acidity of the three catalysts. Accordingly, it may be that increased calcination temperatures have a greater impact on Lewis acid sites than Brønsted acid sites.

Example 11

Temperature Dependence of Total Acidity

To further assess the effect of calcination temperature on Lewis and Brønsted acidity, alumina-silica catalysts prepared at calcination temperatures of room temperature (control), 500° C., and 700° C. were exposed to pyridine vapors as described in Example 10. Catalysts were then exposed to increasing temperatures and infrared spectra at 1455 $cm^{-1}$ and 1540 $cm^{-1}$ were recorded as a function of temperature. A final spectrum was recorded at 400° C. (i.e., ">400° C."). For the 1455 $cm^{-1}$ and 1540 $cm^{-1}$ peaks for each catalyst, the change in absorbance in going from temperature 1 to temperature 2 as a fraction of the total absorbance at the initial temperature was determined. This provides an indication of the relative number of acid sites as a function of acid strength. Results are shown in Tables 4 and 5 and FIGS. 5 and 6.

Figure 5:
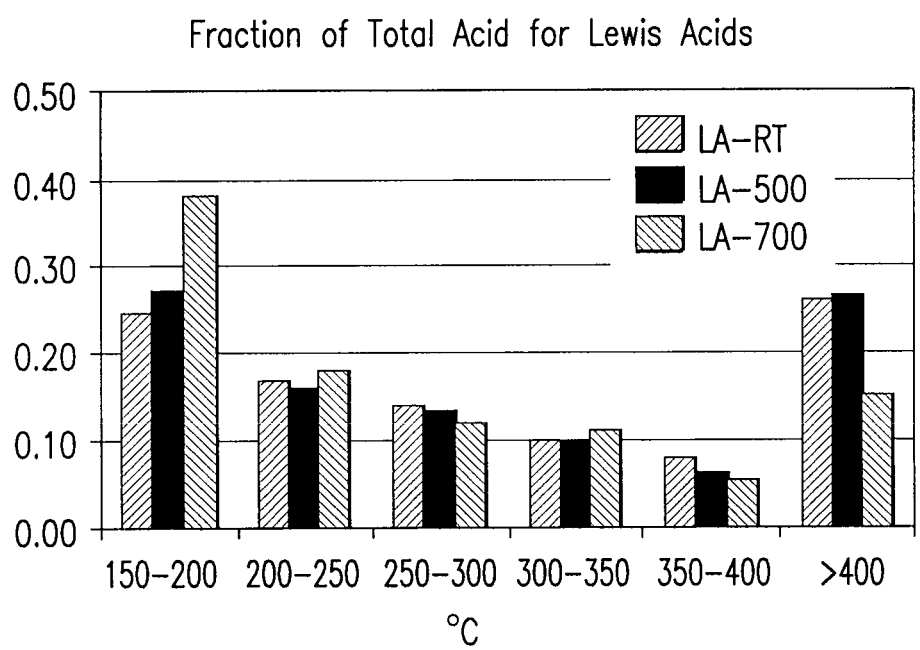
FIG. 5 is a bar graph illustrating the relative fraction of catalyst coordinated to pyridine (e.g., at Lewis acid sites) at various temperatures according to specific example embodiments of the disclosure.

In this assay, temperature provides an approximation of binding strength: the higher the temperature, the stronger the acid site binding pyridine. As shown in FIG. 5, the specific example catalyst calcined at 700° C. had a higher fraction of its acid sites coordinately bound to pyridine at low temperature (150-200° C.) than the other specific example catalyst or the control. Thus, it had a higher fraction of relatively weak Lewis acid sites. Likewise, since it had a lower fraction of its acid sites bound to pyridine at higher temperatures (350-400° C. and >400° C.), the specific example catalyst calcined at 700° C. had a lower fraction of relatively strong Lewis acid sites.

TABLE 4

Fractional Basis-Lewis Acid Strength Distribution

| Temperature | LA-700 | LA-500 | LA-RT |
|---|---|---|---|
| 150-200° C. | 0.382 | 0.272 | 0.247 |
| 200-250° C. | 0.181 | 0.161 | 0.172 |
| 250-300° C. | 0.121 | 0.136 | 0.140 |
| 300-350° C. | 0.111 | 0.101 | 0.102 |
| 350-400° C. | 0.055 | 0.064 | 0.008 |
| 400° C. | 0.151 | 0.266 | 0.266 |

Figure 6:
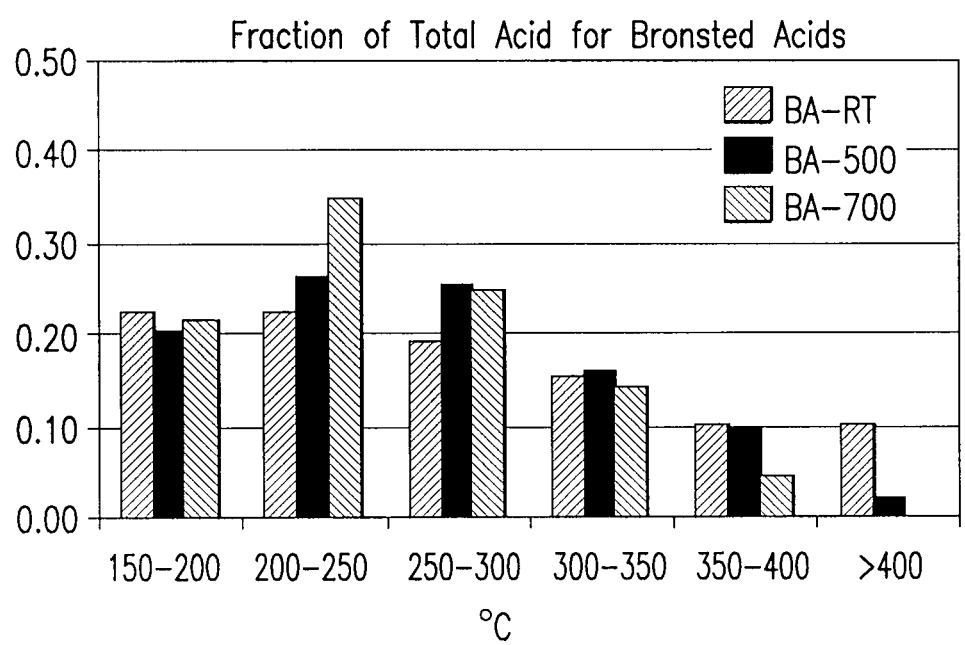
FIG. 6 is a bar graph illustrating the relative fraction of catalyst with pyridinium ions (e.g., Brøonsted acid sites) at various temperatures according to specific example embodiments of the disclosure.

Similarly, the specific example catalyst calcined at 700° C. had a higher fraction of weaker Brønsted acid sites and a lower fraction of stronger Brønsted acid sites (350-400° C. and >400° C.) than the specific example catalyst calcined at 500° C. or the control (FIG. 6).

TABLE 5

Fractional Basis-Brønsted Acid Strength Distribution

| Temperature | BR-700 | BR-500 | BR-RT |
|---|---|---|---|
| 150-200° C. | 0.217 | 0.203 | 0.224 |
| 200-250° C. | 0.348 | 0.263 | 0.224 |
| 250-300° C. | 0.248 | 0.255 | 0.192 |
| 300-350° C. | 0.143 | 0.159 | 0.155 |
| 350-400° C. | 0.043 | 0.100 | 0.102 |
| 400° C. | 0.000 | 0.020 | 0.102 |

Example 12

Preparation of Silica Alumina SiAl-A13, 13 wt % Al$_2$O$_3$ Using a Sol-Gel Method The preparation was carried out under nitrogen and exclusion of moisture. A 250 mL round-bottomed flask containing a magnetic Teflon-coated stir bar was charged with 50 mL of dry 2-propanol and 17.33 g (0.0832 mol) of tetraethoxysilane (TEOS, Aldrich). The mixture was then heated to 80° C., and 2.99 g (0.0146 mol) of solid aluminum isopropoxide (Aldrich) was added in one single step. The clear, homogeneous mixture was stirred for two hours at this temperature, cooled down to room temperature and then placed in an ice bath for further cooling to ≤5° C. Separately, 8 mL of acidified water (1.25 mL of 2M HNO$_3$/100 mL) was also cooled to ≤5° C. Next, the reaction mixture was hydrolyzed by slowly adding the acidified H$_2$O, resulting in a clear, homogeneous solution. The mixture was allowed to warm up to room temperature and stirred for another 30 min before it was left standing overnight at room temperature. The clear, homogeneous gel was then removed, dried at 70° C. for eight hours, and then calcined at 120° C. (2 h), 550° C. (4 h), and 700° C. (10 h) under flowing air (5 L/min). Yield: 5.55 g of a white, glassy material.

Example 13

Preparation of Silica Alumina SiAl-A27.5, 27.5 wt % Al$_2$O$_3$ Using a Sol-Gel Method The preparation was carried out under nitrogen and exclusion of moisture. A 250 mL round-bottomed flask containing a magnetic Teflon-coated stir bar was charged with 50 mL of dry 2-propanol, 7.79 g (0.0374 mol) of TEOS, and 10.64 g (0.0302 mol) of di-s-butoxyaluminoxytriethoxysilane (Gelest, Inc.). The clear, homogeneous mixture was heated to 80° C., stirred for another two hours at this temperature and then cooled down to room temperature. The mixture was then cooled to 5° C., and hydrolyzed by adding 8 mL of acidified H$_2$O (i.e., example 1). After standing at room temperature overnight, the clear gel was dried at 70° C. for eight hours, and then calcined (dried) at 120° C. (2 h), 550° C. (4 h), and 700° C. (10 h) under flowing air (5 L/min). Yield: 5.13 g of a white, glassy material.

Example 14

Catalytic Activity

Reaction Conditions: 5.0 g Aminal (5:1); 0.5 g catalyst; 60° C./4 h; 95° C./2 h. Product analysis (gas chromatography) in wt %. SiAl-A13, Si/Al=5.68 (13 wt % Al$_2$O$_3$): Aniline, 60.39; OABA, 1.68; 2,4'-MDA, 3.45; PABA, 3.33; 4,4'-MDA, 24.54. SiAl-A27.5, Si/Al=2.24 (27.5 wt % Al$_2$O$_3$): Aniline, 62.17; OABA, 1.57; 2,4'-MDA, 3.34; PABA, 0.34; 4,4'-MDA, 28.95.

Example 15

Preparation of Silica Alumina SiAl-A27.5 Using a Sol-Gel Method

A variety of amorphous silica-alumina catalysts with Al$_2$O$_3$ contents varying from 0 wt % to 46 wt % were prepared from silicon and aluminum alkoxides following the general procedure described below for SiAl-A27.5 (SiO$_2$Al$_2$O$_3$ (27.5); 27.5 wt % Al$_2$O$_3$, Si/Al=2.24; SiO$_2$/Al$_2$O$_3$=4.48), Scheme 1.

Scheme 1.

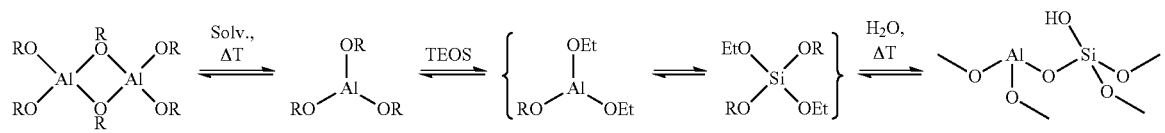

The preparation of a pre-hydrolysis mixture is carried out under argon and exclusion of moisture. A typical preparation is carried out in 50 mL 2-propanol using an equimolar concentration (Si+Al=97.8 mmol). The procedure described below allows for the preparation of 5-6 g of final (calcined) material. A 250 mL round-bottomed flask containing a magnetic, Teflon-coated stir bar is purged with argon for 15 min. Next, 50 mL of 2-propanol are added to the flask at room temperature. Separately, 7.79 g (0.0374 mol) of TEOS, Si(OEt)$_4$, and 10.64 g (0.0302 mol) of di-s-butoxyaluminoxytriethoxysilane, (s-C$_4$H$_9$)$_2$AlO—Si(OC$_2$H$_5$)$_3$, are mixed in a 40 mL sample vial and added to the round-bottomed flask with stirring. The flask is then fitted with a reflux condenser, connected to a bubbler, and lowered into the oil bath. The mixture is allowed to warm up to 80° C. and stirred for 2 h at this temperature, then cooled to room temperature with stirring (~30 min). Next, the mixture is transferred into a 150 mL plastic cup with lid and placed in an ice bath and cooled ≤5° C. with stirring. Separately, 8 mL of the H$_2$O/HNO$_3$ solution (1.25 mL 2M HNO$_3$ diluted to 100 mL) is placed in a second sample vial and also cooled to ≤5° C. The cold H$_2$O/HNO$_3$ solution is then added slowly to the reaction mixture in the plastic cup using a disposable plastic pipette. The solution should be clear and colorless after the addition. The reaction mixture is then removed from the ice bath and allowed to warm up to room temperature with stirring, and the clear, homogeneous mixture is left standing overnight at room temperature. The solid, clear gel is then transferred into a porcelain dish and dried at 75° C. for 24 hours under circulating air. The dry gel is then crushed and homogenized, and calcined under flowing air (5.0 L/min): 2 h/240° C.; 2 h/350° C.; 4 h/550° C.; overnight/700° C. This process yielded 5.50 g (white solid).

Example 16

Davicat 135 (Lot #0109, SIAL 3113)

The material (DAVICAT SIAL 3113), SiO$_2$, 84.9%; Al$_2$O$_3$, 14.4%; Density, 0.5 g/cc; Pore Volume, 0.76 cc/g; BET Surface Area, 573 m$^2$/g, was obtained from WR GRACE & CO. It was calcined at 700° C. under flowing air (5 L/min) prior to catalytic evaluation.

Example 17

Zeolites LZ20 (Lot #15228-65, $SiO_2/Al_2O_3$~6); and LZ20M (Dealuminated LZ20, Lot #7313-33, $SiO_7/Al_2O_3$~20

Dealuminated zeolite Y prepared in the presence of moisture was found to be active for aminal rearrangement, but appeared to be deactivated relatively quickly. Zeolytic materials LZ20 and LZ20M (FAU) were tested to determine what impact anhydrous pre-treatment and reaction conditions may have on activity.

Example 18

Tube-Furnace Drying of the Pre-Calcined (700° C.) Materials

The catalytic activity of materials described in Examples 15-17 was tested in the absence of air and moisture. Specifically, 2-3 g samples of each material was dried under flowing nitrogen (100 mL/min) at 700° C. for 16 hours. The materials were cooled to RT under flowing nitrogen, and then transferred into a Vacuum Atmospheres dry box.

Example 19

Aminal (2:1, N,N'-Dianilinomethane) Preparation

The preparation was carried out under an inert gas atmosphere (argon). 3000 g aniline (distilled over Zn powder) was placed in a 5 L round-bottomed flask (three-neck), equipped with drop funnel, thermometer, and stir bar and cooled to 5° C. using an ice bath. 525 g formalin solution (37% formaldehyde in $H_2O$) was then added to the aniline with stirring over 30 min, keeping the temperature below 10° C.

The mixture was then allowed to warm up to room temperature and stirred for another four hours. The mixture was then placed in a separatory funnel under argon and left standing overnight at room temperature. The organic phase was then separated and dried over 120 g of anhydrous $MgSO_4$. The final product, containing the 2:1 aminal in excess aniline (total aniline to formaldehyde ratio of 5:1), was used for catalyst evaluation in batch reactions. A portion of the aminal/amiline was transferred into a Vacuum-Atmospheres dry box for catalytic testing under exclusion of air and moisture.

Example 20

Preparation of the PABA (N-(p-Aminobenzyl)Aniline) Synthesis Solution for Catalyst Evaluation A 500 mL round-bottomed flask, equipped with a reflux condenser and thermometer was charged with 233 g of aminal/aniline solution (5:1 molar ratio of aniline to formaldehyde), and 12.0 g of zeolite Y (LZ20M) was added with stirring. The mixture was heated to 45° C. and kept at this temperature for 4-5 hours, depending on the reaction's progress. The reaction was monitored by calibrated GC and nearly complete conversion of the aminal was indicated by a constant level of PABA which was reached after approximately 4.5 hours. The catalyst was removed by vacuum filtration, and the clear, yellow liquid was stored over a 4 Å molecular sieve (Grade 514, 8-12 mesh) overnight at room temperature. The final content of PABA was determined by GC analysis. A portion of the PABA synthesis solution was transferred into a Vacuum-Atmospheres dry box for catalytic testing under exclusion of air and moisture.

Example 21

Catalyst Evaluation (Batch Reactions)

Between 0.1-0.5 g of solid catalyst (examples 1-4, either calcined under air or calcined and dried in the tube furnace) was placed in a 25 mL flask containing a magnetic stir bar. Next, 5.0 g of the PABA synthesis solution (example 6) was added, the mixture was heated to 95° C. and stirred for four hours at this temperature. Aliquots of reaction solution were removed every 30 min, filtered through a syringe filter and analyzed by GC. The catalyst testing protocol was carried out under air as well as under exclusion of air and moisture (drybox). The catalytic activity data comparing both testing protocols is summarized in Table 1 and FIG. 7. More specifically, Table 1 contains a comparison of air-calcined and tube furnace-dried catalysts in the aminal to methylenedianiline rearrangement reaction. Reaction conditions included aminal/aniline (5:1 molar ratio of aniline to formaldehyde), 5.0 mL; solid acid catalyst, 14/30 mesh, 0.1-0.5 g; (1) T=60° C./2 h, (2) T=95° C./4 h; 1atm Ar. Catalytic evaluation of tube-furnace dried samples was carried out in a Vacuum-Atmospheres dry box.

Figure 7:
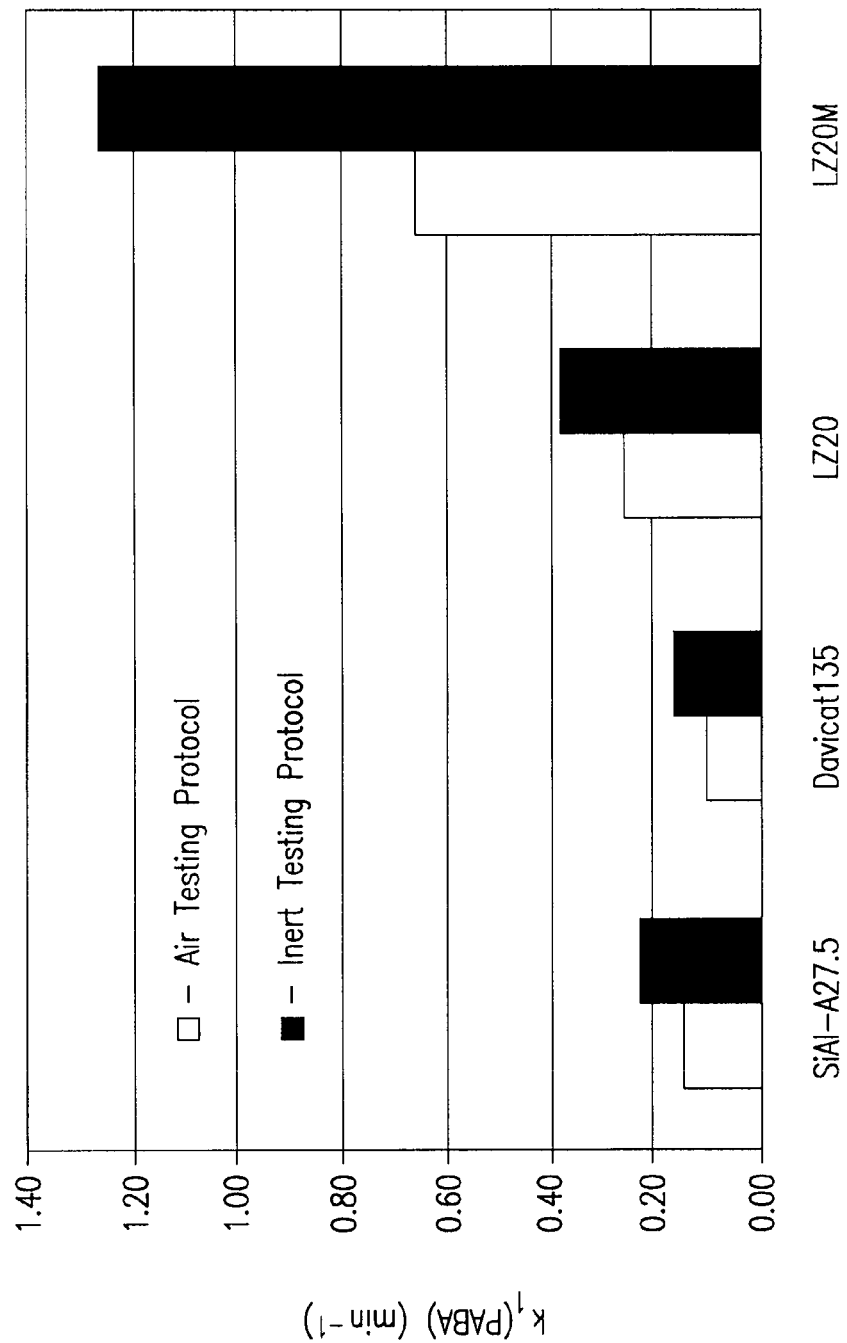
FIG. 7 is a bar graph illustrating the catalytic activity of various air calcined catalysts run under less than anhydrous conditions and tube furnace-dried catalysts run under anhydrous conditions in the aminal to methylenedianiline rearrangement reaction according to specific example embodiments of the disclosure.

FIG. 7 contains a comparison of air-calcined and tube furnace-dried catalysts in the aminal to methylenedianiline rearrangement reaction. Reaction conditions included PABA synthesis solution (5:1 molar ratio of aniline to formaldehyde), 5.0 mL; solid acid catalyst, 14/30 mesh, 0.5 g; T=85° C./4 h; 1 atm Ar. Catalytic evaluation of the tube-furnace dried samples was carried out in a Vacuum-Atmospheres dry box.

TABLE 6

Comparison of Air-Calcined and Tub Furnace-Dried Catalysts

| Catalyst[1] | Protocol[2] | Products[3] | | | | | Catalyst Amount (g) | $k_1$(PABA) $(min^{-1})$[4] |
| | | 4,4'-MDA (wt %) | 2,4'-MDA (wt %) | OABA (wt %) | PABA (wt %) | Oligom. (wt %) | | |
| --- | --- | --- | --- | --- | --- | --- | --- | --- |
| SiA1-A27.5 | Air | 31.76 | 3.88 | 1.63 | 0.63 | 7.98 | 0.5157 | 0.1459 |
| | Inert | 16.14 | 2.31 | 1.99 | 11.28 | 7.58 | 0.1040 | 0.2279 |
| Davicat 135 | Air | 30.38 | 3.92 | 1.76 | 1.41 | 5.62 | 0.5174 | 0.1019 |
| | Inert | 14.82 | 2.21 | 1.99 | 12.94 | 5.41 | 0.1260 | 0.1604 |

TABLE 6-continued

Comparison of Air-Calcined and Tub Furnace-Dried Catalysts

| Catalyst[1] | Protocol[2] | Products[3] | | | | | Catalyst Amount (g) | $k_1$(PABA) $(min^{-1})$[4] |
|---|---|---|---|---|---|---|---|---|
| | | 4,4'-MDA (wt %) | 2,4'-MDA (wt %) | OABA (wt %) | PABA (wt %) | Oligom. (wt %) | | |
| LZ20 | Air | 23.96 | 1.15 | 1.84 | 5.86 | 4.67 | 0.1127 | 0.2584 |
| | Inert | 28.58 | 1.31 | 1.68 | 4.29 | 6.62 | 0.1130 | 0.3745 |
| LZ20M | Air | 34.12 | 1.38 | 1.65 | 0.67 | 1.79 | 0.1131 | 1.2607 |
| | Inert | 36.87 | 1.54 | 0.39 | 0.12 | 4.36 | 0.1050 | 1.2607 |

[1]All materials were calcined at 700° C. in air prior to evaluation.
[2](1) Air Protocol: Catalysts were used for evaluations after calcination at 700° C. in air. (2) Catalysts were used for evaluations after calcination at 700° C. in air followed by drying under flowing $N_2$ in a tube furnace, catalytic testing was performed in a Vacuum-Atmospheres dry box.
[3]Produce distribution by GC analysis. [Oligomers] = 100% − Σ[4,4'-MDA + 2,4'-MDA = OABA + PABA]
[4]First order rate constant of PABA disappearance under the employed reaction conditions. $k_1$(PABA) = {SLOPE(ln [PABA]/time}/cat./[PABA/aniline]}; $\{min^{-1}\}$.

Example 22

Figure 8:
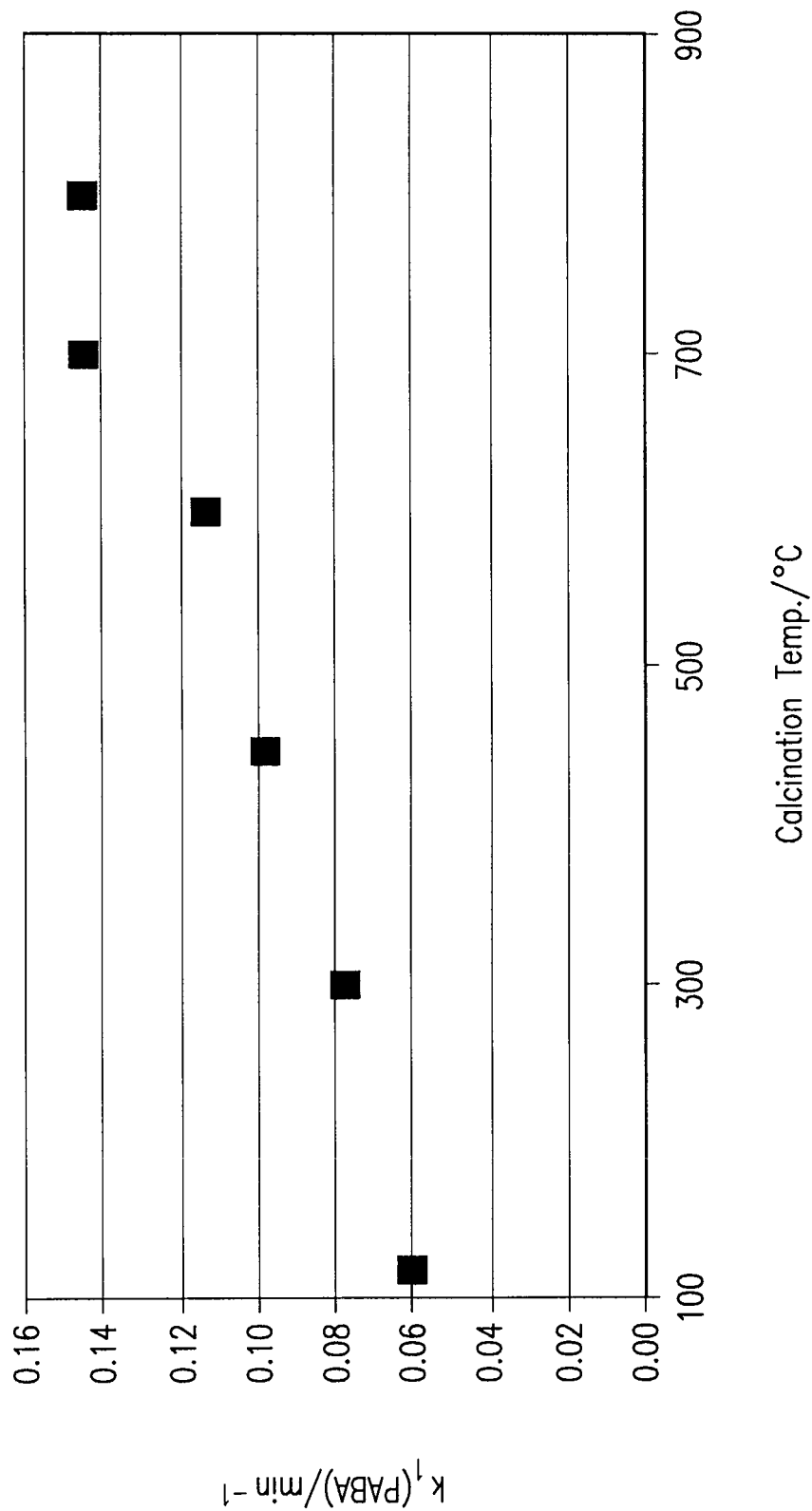
FIG. 8 is a graph illustrating the catalytic activity for SiAl-A27.5 in the aminal to methylenedianiline rearrangement reaction as a function of calcination temperature (120° C.-800° C.), according to specific example embodiments of the disclosure, run under less than anhydrous conditions.

Catalyst Evaluation (Batch Reaction): SiAl-A27.5, Calcination Temperature/Activity Study The catalytic activity of SiAl-A27.5 was evaluated vs. the calcination temperature. Sample calcination and activity measurements were carried out according to example 7 using an air-calcined sample of SiAl-A27.5 as the solid catalyst. A significant activity increase was found with increasing calcination temperature. The activity data for the sample calcined at 800° C. is shown below and illustrated in FIG. 8 (PABA synthesis solution (5:1 molar ratio of aniline to formaldehyde), 5.0 mL; solid acid catalyst, 14/30 mesh, 0.5 g; T=95° C./4 h; 1 atm Ar.).

800° C.: Product composition (95° C., 4 h of reaction time): 4,4'-MDA: 23.8 wt %; 2,4'-MDA: 2.1 wt %' N-o-Aminobenzyl aniline (OABA): 1.7 wt %; N-p-Aminobenzyl aniline (PABA): 7.1 wt %; Trimers and heavy components: 13.4 wt %.

What is claimed is:

1. A process for producing a methylenedianiline or a mixture of methylenedianiline and its higher homologues, said process comprising:
    contacting aniline and formaldehyde under conditions that permit formation of an aminal;
    contacting a catalyst composition with the aminal to form the methylenedianiline, wherein the catalyst composition comprises an anhydrous solid acid silica-metal oxide catalyst.

2. A process according to claim 1, wherein the mole ratio of metal oxide to silica is from about 0.01 to about 0.5.

3. A process according to claim 1, wherein the metal oxide is selected from the group consisting of $Al_2O_3$, $TiO_2$, $GeO_2$, $SnO_2$, $ZrO_2$, $B_2O_3$, $Nb_2O_5$, $Ta_2O_5$, $V_2O_5$, $MoO_3$, $WO_3$, and combinations thereof.

4. A process according to claim 1, wherein (a) the metal oxide is $Al_2O_3$ and (b) the solid acid silica-metal oxide catalyst (i) is substantially free of a binding agent and (ii) has an $Al_2O_3/SiO_2$ weight ratio of from about 0 to about 1.

5. A process according to claim 4, wherein the solid acid silica-metal oxide catalyst has an $Al_2O_3/SiO_2$ weight ratio of from about 0.1 to about 0.5.

6. A process according to claim 1, wherein the catalyst composition further comprises a binding agent.

7. A process according to claim 6, wherein the solid acid silica-metal oxide catalyst comprises from about 5 wt % to about 60 wt % $Al_2O_3$.

8. A process according to claim 1, wherein the methylenedianiline formed comprises at least about 40 weight percent 4,4'-methylenedianiline.

9. A process according to claim 1, wherein the conditions (ii) to rearrange the aminal to form the methylenedianiline comprise a temperature of from about 60° to about 120° C.

10. A process according to claim 1, wherein the conditions (ii) to rearrange the aminal to form the methylenedianiline comprise a catalyst loading of from about 2 wt % to about 15 wt % for a slurry process.

11. A process according to claim 1, wherein the contacting aniline and formaldehyde comprises contacting aniline and formaldehyde at a molar ratio of aniline to formaldehyde of from about 2/1 to about 5/1.

12. A process according to claim 1, wherein the contacting the aminal and the catalyst comprises contacting the aminal and the catalyst in multiple temperature zones, using either multiple fixed bed reactors or a fixed bed reactor or reactors with multiple temperature zones.

13. A process according to claim 12, wherein the multiple temperature zones comprise a first zone having a temperature of 40-80° C. and a second zone having a temperature range of 80-150° C.

14. A process according to claim 13, wherein the multiple temperature zones further comprise a third temperature zone of 100-150° C.

* * * * *